United States Patent
Semen

(10) Patent No.: US 6,800,228 B1
(45) Date of Patent: ***Oct. 5, 2004

(54) STERICALLY HINDERED PHENOL ANTIOXIDANT GRANULES HAVING BALANCED HARDNESS

(75) Inventor: John Semen, Baton Rouge, LA (US)

(73) Assignee: Albemarle Corporation, Richmond, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/528,675

(22) Filed: Mar. 20, 2000

Related U.S. Application Data

(63) Continuation-in-part of application No. 09/204,121, filed on Dec. 2, 1998, now Pat. No. 6,126,863, which is a continuation-in-part of application No. 09/203,941, filed on Dec. 2, 1998, now Pat. No. 6,126,862, which is a continuation-in-part of application No. 09/158,588, filed on Sep. 22, 1998, now Pat. No. 6,056,898.

(51) Int. Cl.[7] ......................... B29C 67/00; B29C 67/02; C09K 15/08
(52) U.S. Cl. ...................... 264/109; 264/115; 264/117; 264/118; 252/404; 252/407; 252/400.24; 252/182.29
(58) Field of Search .............................. 252/404, 407, 252/400.24, 400.23, 182.29; 264/140, 141, 128, 122, 120, 109, 142, 143, 144, 145, 115, 117, 118; 428/402

(56) References Cited

U.S. PATENT DOCUMENTS

| | | | |
|---|---|---|---|
| 3,664,961 A | 5/1972 | Norris | 252/99 |
| 3,781,397 A | 12/1973 | Gauer et al. | |
| 4,038,477 A | 7/1977 | Inoue et al. | 528/487 |
| 4,077,902 A | 3/1978 | Moser et al. | |
| 4,098,858 A | 7/1978 | Ten Broeck | 264/117 |
| 4,134,725 A | 1/1979 | Buchel et al. | 8/79 |

(List continued on next page.)

FOREIGN PATENT DOCUMENTS

| | | |
|---|---|---|
| DE | 2922378 | 12/1980 |
| EP | 0 403431 A2 | 6/1989 |
| EP | 0514 784 A1 | 5/1992 |
| EP | 0 525 200 A1 | 9/1992 |
| EP | 0 719 824 A2 | 12/1995 |
| WO | WO 97/09376 | 3/1997 |
| WO | WO 01 70869 A2 | 9/2001 |

Primary Examiner—Joseph D. Anthony
(74) Attorney, Agent, or Firm—Edgar E. Spielman, Jr.

(57) ABSTRACT

Sterically hindered phenol antioxidant additive granules are formed from a paste comprising an organic processing agent comprising a friability reduction agent. The friability reduction agent preferably is an alcohol, more preferably an alkanol having up to about 8 carbon atoms, most preferably methanol, ethanol, and/or isopranol. After drying, the granules consist essentially of the sterically hindered phenol antioxidant additive system. The granules have a balanced hardness that provides sufficient abrasion resistance while permitting ready dispersion into a polymer host.

20 Claims, 1 Drawing Sheet

U.S. PATENT DOCUMENTS

| | | | | |
|---|---|---|---|---|
| 4,357,449 A | * | 11/1982 | Yi | 526/74 |
| 4,438,263 A | | 3/1984 | Morse | 536/56 |
| 4,442,017 A | | 4/1984 | Blumberg et al. | |
| 4,446,086 A | | 5/1984 | Molenaar et al. | 264/118 |
| 4,510,073 A | | 4/1985 | Hara et al. | 252/383 |
| 4,560,527 A | | 12/1985 | Harke et al. | 264/500 |
| 4,594,444 A | | 6/1986 | Orban | 560/67 |
| 4,670,181 A | | 6/1987 | Mollinger et al. | 252/186.25 |
| 4,716,244 A | | 12/1987 | Orban | 560/75 |
| 4,761,248 A | | 8/1988 | Clift | 252/527 |
| 4,764,428 A | | 8/1988 | Gloyer | |
| 4,902,210 A | | 2/1990 | Shibata | 425/6 |
| 4,943,301 A | | 7/1990 | Nagle et al. | 23/313 |
| 4,957,956 A | | 9/1990 | Neri et al. | 524/120 |
| 5,006,284 A | | 4/1991 | Gahan | 264/9 |
| 5,011,640 A | | 4/1991 | Zanchetta | 264/69 |
| 5,030,400 A | | 7/1991 | Danielsen et al. | 264/101 |
| 5,117,040 A | * | 5/1992 | Marutani et al. | 560/75 |
| 5,124,100 A | | 6/1992 | Nishii et al. | 264/82 |
| 5,196,565 A | | 3/1993 | Ross | 560/55 |
| 5,240,642 A | | 8/1993 | Neri et al. | 252/399 |
| 5,290,495 A | | 3/1994 | Numadate et al. | 264/141 |
| 5,292,461 A | | 3/1994 | Juch et al. | 264/37 |
| 5,318,733 A | | 6/1994 | Carduck et al. | 264/15 |
| 5,348,695 A | | 9/1994 | Ploumen et al. | 264/42 |
| 5,382,377 A | | 1/1995 | Raehse et al. | 252/174 |
| 5,460,765 A | | 10/1995 | Derdall et al. | 264/117 |
| 5,597,857 A | | 1/1997 | Thibaut et al. | 524/400 |
| 5,700,497 A | | 12/1997 | Stone et al. | 425/222 |
| 5,844,042 A | | 12/1998 | Neri et al. | 523/223 |
| 5,846,656 A | | 12/1998 | Dunski | 428/502 |
| 6,056,897 A | * | 5/2000 | Pallini et al. | 252/399 |
| 6,056,898 A | | 5/2000 | Semen | |
| 6,596,198 B1 | * | 7/2003 | Semen | 252/400.24 |

* cited by examiner

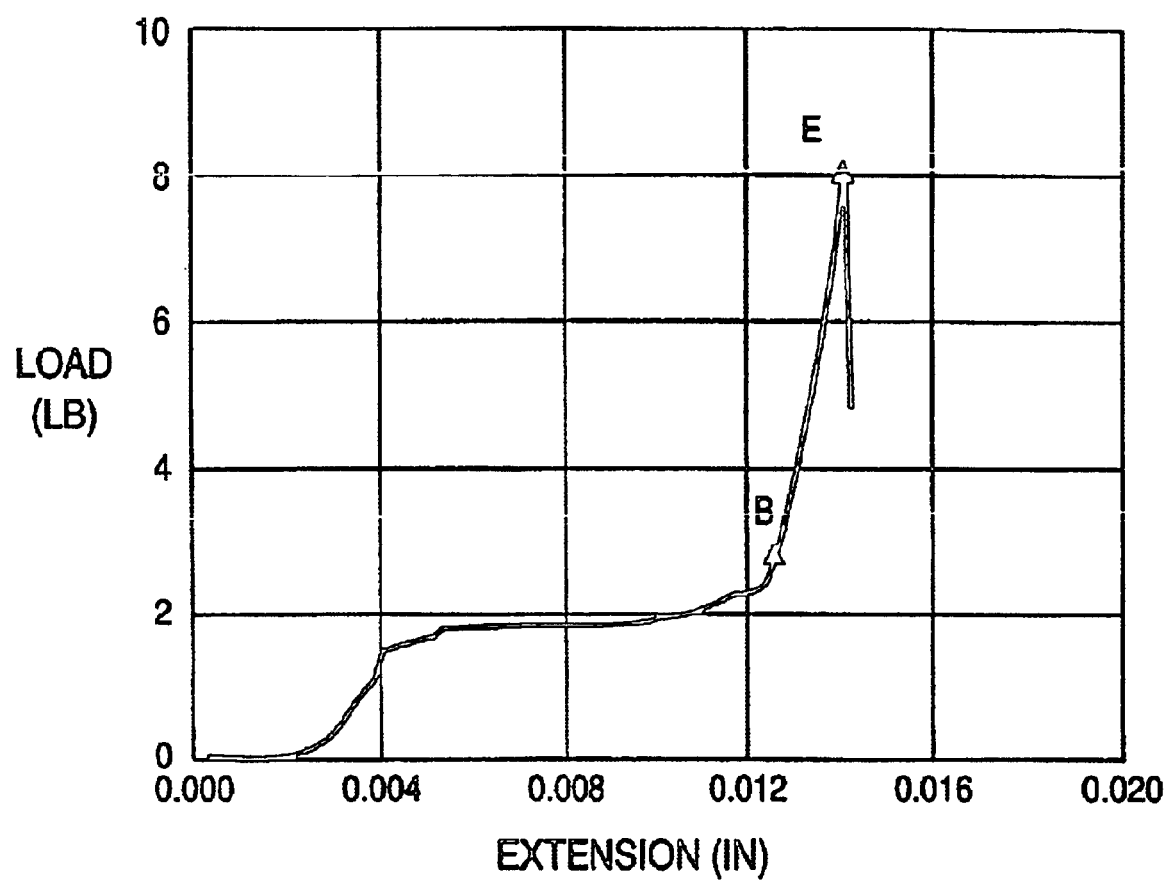

STERICALLY HINDERED PHENOL ANTIOXIDANT GRANULES HAVING BALANCED HARDNESS

The present application is a continuation-in-part of the following applications: application Ser. No. 09/158,588, filed Sep. 22, 1998; now U.S. Pat. No. 6,056,898 application Ser. No. 09/204,121, filed Dec. 2, 1998; now U.S. Pat. No. 6,126,863 and application Ser. No. 09/203,941, filed Dec. 2, 1998, now U.S. Pat. No. 6,126,862.

FIELD OF THE INVENTION

The present invention relates to the use of a paste to make inherently coherent dried granules of sterically hindered phenol antioxidants. The dried granules have a balanced hardness suitable for both handling and incorporation into a polymer composition. The granules may be agglomerates, which typically are spherical in shape, or they may be cylindrical or elongated pellets.

BACKGROUND OF THE INVENTION

Organic polymers, in particular polyolefins such as polyethylene and polypropylene, commonly are known as "plastics." Various additive systems are used during the processing of plastics in order to assure that the plastic product has long term stability and desired service properties. Additives and stabilizers prevent the plastic product from being damaged by light, heat, and by residues of the catalyst system used to produce the plastic.

The additives and stabilizers may be used individually, or in an additive "system" that includes a mixture of components. Common additive systems include sterically hindered phenol antioxidants in combination with a secondary phosphite antioxidant and/or an acid neutralizer.

Sterically hindered phenol antioxidants generally are fine powders that present dusting and other handling problems, as well as separation tendencies that cause metering difficulties. In the past, these problems have been solved by adding extraneous binders to the additive system. Exemplary binders used for such purpose include fatty acids and their salts, such as calcium stearate. The disadvantage of using an extraneous binder is that the binder remains as a contaminant in the final additive system.

Additive systems are needed which solve the handling problems for sterically hindered phenols, but which do not introduce contaminats into the final additive system.

SUMMARY OF THE INVENTION

The present invention solves the foregoing problem by providing a compound comprising
a powder comprising an additive system comprising at least one sterically hindered phenol antioxidant; and, an organic processing agent comprising at least one friability reduction agent. The invention also is directed to a compound consisting essentially of one or more dried granules consisting essentially of an additive system comprising at least one sterically hindered phenol.

BRIEF DESCRIPTION OF THE DRAWINGS

FIG. 1 shows a graph of the balanced hardness for pellets made according to the present invention as a factor of load versus time, with the maximum attained load normalized by the length dimension of the granule.

DETAILED DESCRIPTION OF THE INVENTION

The granules of sterically hindered phenol antioxidant of the present invention may have any suitable form, such as agglomerates or pellets. The granules have a "balanced hardness," defined as a hardness sufficient to provide adequate resistance to abrasion during handing ("abrasion resistance") and also ready homogeneous dispersability in a host plastic material using conventional dispersing systems, such as a compounding extruder. The balanced hardness is difficult to measure when the granules are agglomerates, or spherical in shape. However, the balanced hardness of pellets may be measured, quantified, and varied to suit particular processing requirements.

Typically, granule coherence is achieved using an "extraneous binder." An "extraneous binder" is defined herein as a material that does not function as a component of the additive system once dispersed in the host plastic, but which does assist in achieving granule coherence and a suitable granule hardness. An "extraneous binder" typically provides coherence to a material by "melting" to hold the granule together after processing. Instead of using an extraneous binder, the present invention provides coherence and regulates balanced hardness of the granules by regulating the composition of the "organic processing agent" used to process the sterically hindered phenol into granules. More specifically, the invention uses an organic processing agent which, at least in part, comprises a friability reduction agent, most preferably an alcohol. Preferably, the process of the present invention is performed at a temperature that is sufficiently low to avoid melting any component of the additive system, including the sterically hindered phenol.

The Organic Processing Agent

The organic processing agent comprises the friability reduction agent and also may comprise a traditional solvent. The organic processing agent has a sufficiently low vaporization point or boiling temperature to evaporate from the granules before the sterically hindered phenol begins to melt or degrade. The composition and vaporization point of the organic processing agent thus will vary with the type and the melting point of the sterically hindered phenol being processed.

A. The Friability Reduction Agent

The "friability reduction agent" is defined as a fluid in which a given sterically hindered phenol has sufficient dispersability to form a paste and to be processed into granules, but insufficient solubility to dissolve the phenol sufficiently to form a "glue" phase. Without limiting the invention to a particular mechanism of action, molecules of the sterically hindered phenol are believed to become sufficiently "dispersed" in the friability reduction agent that, upon drying, the molecules of the sterically hindered phenol "precipitate out" of or deposit from the friability reduction agent, forming an essentially amorphous phase. The majority of the sterically hindered phenol in the granules produced according to the present invention is crystalline in nature. About 1 wt. % to about 5 wt. % of the sterically hindered phenol found in the granules comprises an amorphous phase. The molecules of phenol forming the amorphous phase are believed to be the precipitated molecules of the sterically hindered phenol, which are believed to form bonds that act as a "bridging agent" to provide inherent coherence and "balanced hardness" to the dried granules. The coherence is "inherent" because it is produced by components of the additive system, itself. Coherence does not require the use of an extraneous binder.

Suitable friability reduction agents include, but are not necessarily limited to alcohols, preferably alkanols, most preferably normal alkanols and their equivalents. Preferred friability reduction agents are alcohols of the formula ROH wherein R is an alkyl group having from about 1 to about 8 carbon atoms, preferably from about 1 to about 4 carbon atoms. Preferred alcohols include, but are not necessarily limited to: methanol, with a boiling point of 148.5° F. (64.7° C.); ethanol, with a boiling point of 172.5° F. (78° C.); and isopropanol, with a boiling point of 179.5° F. (82° C.). Isopropanol is a most preferred alcohol, and a most preferred friability reduction agent.

B. The Solvent

As used herein, the term "solvent" is defined as an organic solvent capable of dissolving at least about 2 g of sterically hindered phenol per 100 mL of solvent. Examples of such "solvents" include, but are not necessarily limited to methylene chloride, with a boiling point of 104° F. (40° C.); chloroform, with a boiling point of 142° F. (61° C.); toluene, with a boiling point of 230° F. (110° C.); acetone with a boiling point of 133° F. (56° C.); methyl ethyl ketone, with a boiling point of 176° F. (80° C.); xylene, with a boiling point of 284° F. (140° C.); cyclohexane, with a boiling point of 177° F. (80.7° C.); styrene, with a boiling point of 293° F. (145° C.); methylcyclohexane, with a boiling point of 214° F. (101° C.); hexane, with a boiling point of 156° F. (69° C.); and combinations thereof. Most preferred solvents are cyclohexane, methylethylketone, and combinations thereof.

The sterically hindered phenol readily dissolves in such solvents and produces a "glue" phase, even when the phenol is not melted Upon drying, this "glue phase" typically is very hard, absent some kind of softening treatment. To the extent that the granules contain such a solvent, the resulting "glue" phase increases the balanced hardness of the granules. The organic processing agent of the present invention limits the amount of the glue phase formed during processing by controlling the amount of "solvent" in the "organic processing agent." The solvent is replaced by variable quantities of the "friability reduction agent."

The Sterically Hindered Phenol

Useful sterically hindered phenol antioxidants generally possess a characteristic melting point of from about 50° C. (122° F.) or greater, preferably from about 95° C. (203° F.) or greater, most preferably about 100° C. or greater. The minimum melting point provides a practical limit on the temperature used to dry the granules. Examples of suitable sterically hindered phenols are described below.

The amount of sterically hindered phenol antioxidant in the granules may vary from about 5 weight percent or more, more preferably from about 10 weight percent or more, still more preferably from about 20 weight percent to about 50 weight percent. The granules also may comprise 100 weight percent sterically hindered phenol antioxidant. Other additives, i.e., active components of the blend for the end use application are known, and may be included in any suitable amount, with the proper amount of a given active component of the blend being determinable by those skilled in the art for a given use. Examples of such additives are given below. A preferred additive is from about 15 wt. % to about 85 wt. % of an acid neutralizer. When the granules are formed in admixture with other components, such as a phosphite antioxidant, the agglomerates contain at least about 3 wt. %, preferably at least about 5 wt. %, and most preferably from about 20 wt. % to about 100 wt. % of the sterically hindered phenol.

Manufacture of Granules

For simplicity sake only, the manufacture of the granules and various physical parameters will be discussed with reference to alcohol as the friability reduction agent.

Formation of a Paste

The granules are made from a paste comprising a powder comprising the sterically hindered phenol antioxidant, alone, or in combination with desired additives, which may include another antioxidant. The balanced hardness preferably is produced without incorporating extraneous binders that remain in the granules after drying; however, the friability reduction agents of the present invention may contain one or more extraneous binders. As used herein the term "paste" is defined as a "slurry" with sufficient coherence to process into granules. The paste contains at least about 1 gram of additive powder comprising the sterically hindered phenol antioxidant per about 100 mL of the organic processing agent.

A suitable paste for either agglomeration or pelletization is formed by mixing the following quantities of components in a suitable container or hopper: from (a) about 3 parts by weight organic processing agent to about 97 parts by weight powder, to (b) about 20 parts by weight organic processing agent to about 80 parts by weight powder. The mixture is agitated, e.g., with a spatula or a paddle mixer, until a "paste" forms.

A. Formation of Agglomerates

The term "agglomerate" generally refers to a small, rounded, or spherical body of a sterically hindered phenol antioxidant. Where the paste is used to make agglomerates, at least about 20 weight percent of the organic processing agent must be the friability reduction agent. This is because the friability reduction agent acts as a wetting agent which actually initiates agglomeration, or particle formation. The organic processing agent used for agglomeration also may comprise up to about 80 weight percent of the solvent.

Agglomerates typically are produced in an agglomerator, such as a "pin agglomerator," available from Feeco International (Green Bay, Wis.). Suitable "agglomerates" may be formed using a wide variety of methods and agglomerating equipment well known to those of ordinary skill in the art. Examples include, but are not necessarily limited to those described in the following U.S. Patents, which are incorporated herein by reference: U.S. Pat. Nos. 4,134,725; 4,902, 210; 5,011,640; 5,030,400; 5,124,100; 5,460,765; 5,700, 497.

To form agglomerates, the paste is placed in a container and the container is rotated, typically at about 60 rpm, with a rotoevaporator head. The container is simultaneously "tapped" or tumbled, e.g., using a drum or agglomerator, in order to initiate particle formation. A preferred agglomerator is a "pin agglomerator," available from Feeco International (Green Bay, Wis.). The agglomerated particles are then dried (as described below).

B. Formation of Pellets

The paste preferably is used to form pellets. As used herein, the term "pellet" generally refers to granules made using extrusion techniques. Extrusion techniques typically involve the formation of elongated "spaghetti-like" strands of extruded material, which are broken into pieces to form pellets. As a result, pellets typically are small, columnar or cylindrical bodies. However, pellets may be spherical, or they may have flat surfaces, such as those found in cubes, rectangular parallelpepipeds, etc.

Since the friability reduction agent is not required to "initiate" pellet formation, the organic processing agent used to form pellets may contain less than 20 weight percent of the friability reduction agent. The paste is pressed through a die extruder to form strands, which typically are pelletized as they are extruded. This may be accomplished using a variety of known methods, preferably at a maximized feed rate. Examples of pelleting equipment suitable for adaptation and use in the present invention include, but are not necessarily limited to those described in the following U.S. Patents, which are incorporated herein by reference; U.S. Pat. Nos. 4,446,086; 4,670,181; 4,902,210; 5,292,461. A preferred pellet press is a Kahl Model 14-175 Pellet Press equipped with a die plate containing holes of from about 2 to about 6 mm diameter, preferably about 3 mm diameter, which runs at from about 25 lb/hr to about 150 lb/hr. The length at which the strand-like product breaks after leaving the die is determined by a number of factors, including but not necessarily limited to the composition, the temperature, the extrusion pressure, the speed of the revolutions, and the distance between the cutters and the bottom of the die plate. The press operates at a rotor speed of nominally from about 80 to about 250 rpm, preferably from about 80 to about 100 rpm.

Extrusion through a press preferably occurs at a temperature below that at which solvents in the extrudant vaporize or at which any of the components of the additive system melt. Maximum temperatures may differ slightly for a given system, but a maximum temperature typically is about 70° C. or less. Persons of ordinary skill in the art recognize that a variety of factors affect the temperature of extrusion, including but not necessarily limited to powder composition, rotor speed, feed rate, solvent, type of pellet mill, etc. However, the "aspect ratio," or the ratio of the diameter to the length of the holes in the die plate, is of particular importance. The smaller the "aspect ratio," the cooler the temperature of extrusion. Typically, an aspect ratio of from about 2.5 to about 4 is required to maintain the extrudation process at a temperature of about 70° C. or less.

Drying

After formulation, the agglomerates or pellets ("formed granules") are dried "Drying" of the formed granules involves exposing the formed granules to elevated temperatures which are sufficiently high to evaporate the organic processing agent(s) but sufficiently low to avoid melting of the components in the additive system, including the sterically hindered phenol. The drying temperature may vary depending upon a number of factors, particularly the type of phenol, the other additives found in the granules, and the processing solvent used. Typically, the formed granules are dried for a period of from about 30 minutes to about 6 hours, preferably for about 60 minutes in a forced-air oven operating under an inert atmosphere—preferably nitrogen—at a temperature of from about 50° C. to the melting temperature of the lowest melting additive in the granule, preferably at about 100° C. or less. A vacuum, or partial pressure, also may be used to facilitate drying. A "dried granule" is defined as a granule that has been subjected to sufficient drying to remove the organic processing agent to about 0.1 weight percent or less, depending upon commercial specifications for the dried product.

The dried granules are sieved using an appropriately sized screen to remove fines. Dried agglomerates typically have an average diameter of from about 1 mm to about 10 mm, preferably from about 1 mm to about 5 mm. Dried pellets have (a) an average diameter (x) of from about 1 mm to about 10 mm, preferably from about 2 mm to about 6 mm, most preferably about 3 mm, and (b) an average length of from about 1.5× to about 3×, typically and perhaps preferably 2× to 3×. Whether agglomerates or pellets, the granules generally possess a loose bulk density of from about 400 g/l or greater, with a preferred loose bulk density being from about 500 g/l or greater.

Hosokawa Flowability

For ease of addition to a host plastic, the granules preferably have a high "Hosokawa Flowability" rating. Hosokawa Flowability is a powder flowability rating based on a 0–100 rating scale, with 100 representing ideally perfect powder flow and 0 representing extremely poor powder flow. Hosokawa Flowability of the pellets made according to the present invention preferably is about 70 or greater, more preferably about 80 or greater.

Control over Balanced Hardness

The balanced hardness of both agglomerates and pellets is affected by the quantity of the friability reduction agent used. However, the impact of the friability reduction agent on the balanced hardness of the pellets is measureable. Balanced hardness of pellets is calculated as a factor of load versus time, as seen in FIG. 1, with the maximum attained load normalized by the length dimension of the granule being the balanced hardness for a given composition. As seen in FIG. 1, the x-axis is delineated as a measure of displacement (inches), with the y-axis metered in pounds (lb).

An inverse relationship exists between the balanced hardness of pellets formed using the paste and the quantity of the friability reduction agent used in the organic processing agent. As the concentration of alcohol in the organic processing agent increases, the balanced hardness of the pellets decreases. As the concentration of the alcohol in the organic processing agent decreases, the balanced hardness of the pellets increases. The use of organic processing agents comprising less friability reduction agent creates pellets having maximum hardness and a maximum balanced hardness for a given sterically hindered phenol antioxidant system. The use of organic processing agents comprising only the friability reduction agent creates pellets having maximum softness and a minimum balanced hardness for a given sterically hindered phenol antioxidant system. The organic processing agent controls the balanced hardness even though the organic processing agent eventually is removed from the pellets, typically by drying.

Minimal balanced hardness for the dried pellets comprises from about 5 lb/in or greater. A preferred balanced hardness for pellets is from about 10 lb/in to about 27 lb/in, more preferably from about 15 lb/in to about 25 lb/in. In most polymer processing procedures, a balanced hardness of from at least about 10 lb/in and no greater than about 27 lb/in is desired for convenient handling and ready dispersion in the polymer forming, hot plastic, process. However as handling norms of a particular polymer processing procedure become milder, the minimum useful balanced hardness for the pellets may be as low as about 5 lb/in. Pellets possessing minimum hardness of from about 5 lb/in or greater generally retain adequate mechanical strength or hardness to have sufficient abrasion resistance to preclude dust formation during conveyance into the polymer forming process. The maximum hardness or friability limit of the dried pellets permits the additive package to readily disperse into a given host plastic process, such as processes that require a hardness of from about 27 lb/in or less. The combination of the minimum and maximum hardness over a given operable range comprises the balanced hardness of the sterically hindered phenol antioxidant pellets for limits of a given host plastic process.

Because the balanced hardness of dried pellets bears a relation to the concentration of alcohol in the organic processing agent, pellets may be produce having a specific, targeted balanced hardness. In order to produce pellets having a balanced hardness of from about 10 lb/in to about 27 lb/in, the organic processing agent comprises from about 20 weight percent to about 50 weight percent alcohol. The remainder of the organic processing agent, from about 50 weight percent to about 80 weight percent, is solvent. The balanced hardness may be refined by adjusting the alcohol content during processing. The organic processing agent controls the balanced hardness even though the organic processing agent eventually is removed from the pellets, typically by drying.

As the hardness of the granules increases, it is more difficult and requires more energy to uniformly disperse the additive package found in the granules into the host plastic during extrusion. As more energy is needed, and particularly when the granule hardness is extremely high, specially designed extruders may be required to extrude the host plastic in order to allow an extended resonance time of the additive package in the extruders, or to allow for the use of higher than normal temperatures. In general, as the granule hardness goes up, the ability of the additive package to disperse in the plastic host goes down. The upper limit of the balanced hardness may be varied to fit particular processing needs.

Example of Components of the Additive System

Representative sterically hindered phenol antioxidants suitable for use in the present invention include organic materials useful in the stabilization of polymers such as polyethylene and polypropylene, and preferably comprise the formula (I):

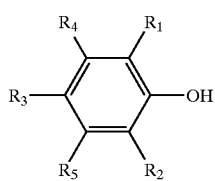

(I)

wherein a $R_1$ and $R_2$ independently are selected from the group consisting of substituents which provide sufficient bulk to prevent conversion of the —OH to an oxygen radical. In a preferred embodiment, $R_1$ and $R_2$ independently are selected from the group consisting of alkyl groups and alkylthioalkyl groups, and $R_3$, $R_4$ and $R_5$ independently are selected from the group consisting of hydrogen, alkyl groups, aromatic groups, and heterocyclic groups comprising compounds selected from the group consisting of nitrogen, oxygen, phosphorous and sulphur. In a preferred embodiment, $R_1$ and $R_2$ independently are selected from the group consisting of hydrogen, methyl groups, ethyl groups and tert-butyl groups, and $R_4$ and $R_5$ are hydrogens. Even more preferably, $R_1$ and $R_2$ independently are selected from the group consisting of methyl groups and tert-butyl groups.

Numerous types of sterically hindered phenol antioxidants may be used in the present invention, including but not necessarily limited to antioxidants comprising alkylated monophenols, alkylthiomethylphenols, hydroquinones, alkylated hydroquinones, tocopherols, hydroxylated thiodiphenyl ethers, alkylidene bisphenols, O-, N-, and S-benzyl compounds, hydroxybenzylated malonates, hydroxybenzyl aromatics, triazines, benzylphosphonates, acylaminophenols, esters of β-(5-tert-butyl-4-hydroxy-3-methylphenyl)propionic acid, esters of β-(3,5-dicyclohexyl-4-hydroxyphenyl)propionic acid, esters of 3,5-di-tert-butyl-4-hydroxyphenylacetic acid, amides of β-(3,5-di-tert-butyl-4-hydroxyphenyl)propionic acid, and combinations thereof.

Examples of these classes of sterically hindered phenol antioxidants include, but are not necessarily limited to the following:

Alkylated monophenols: 2,6-di-tert-butyl-4-methylphenol, 2-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol, 2,4-dimethyl-6-(1'-methyl-undec-1'-yl)-phenol, 2,4-dimethyl-6-(1'-methylheptadec-1'-yl)phenol, 2,4-dimethyl-6-(1'-methyltridec-1'-yl)phenol, and mixtures thereof;

Alkylthiomethylphenols: 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol;

Hydroquinones and alkylated hydroquinones: 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl)adipate.

Hydroxylated thiodiphenyl ethers: 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulfide.

Alkylidene bisphenols: 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylene-bis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris-(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)-butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl-4-hydroxy-2-methylphenyl)pentane.

O-, N- and S-benzyl compounds: 3,5,3',5'-tetra-tert-butyl-4,4'-dihydoxydibenzyl ether, octadecyl 4-hydroxy-3,5-dimethylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl 3,5-di-tert-butyl-4-hydroxybenzylmercapto-cetate.

Hydroxybenzylated malonates: dioctadecyl 2,2-bis 3,5-di-tert-butyl 2-hydroxybenzyl)malonate, dioctadecyl 2-(3-tert-butyl-4-hydroxy-5-methylbenzyl)malonate, didodecylmercaptoethyl 2,2-bis(3,5-di-tert-butyl-4-hydroxybenzyl)malonate, di-[4-(1,1,3,3-tetramethylbutyl)phenyl]-2,2-bis(3,5-di-tert-butyl-4-hydroxybenzyl)malonate.

Hydroxybenzyl aromatic compounds: 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris-(3,5-di-tert-butyl-4-hydroxybenzyl)phenol.

Triazine compounds: 2,4-bisoctylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenyl-propionyl) hexahydro-1,3,5-triazine, 1,3,5-tris(3,5-dicyclohexyl-4-hydroxybenzyl)isocyanurate.

Benzylphosphonates: dimethyl 2,5-di-tert-butyl-4-hydroxybenzylphosphonate; diethyl 3,5-di-tert-butyl-4-hydroxybenzylphosphonate; dioctadecyl-3,5-di-tert-butyl-4-hydroxybenzylphosphonate; dioctadecyl 5-tert-butyl-4-hydroxy-3-methylbenzylphosphonate, calcium salt of monoethyl 3,5-di-tert-butyl-4-hydroxybenzyl phosphonate.

Acylaminophenols: 4-hydroxylauranilide; 4-hydroxystearanilide; octyl N-(3,5-di-tert-butyl-4-hydroxyphenyl)carbamate.

Esters of β-(5-tert-butyl-4-hydroxy-3-methylphenyl) propionic acid, with monohydric or polyhydric alcohols, such as methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl) oxalamide, 3-thiaundecanol, 3-thiapentadecanol, trimethylhexanediol, trimethylolpropane, 4-hydroxymethyl-1-phospha-2,6,7-trioxabicyclo-[2.2.2]octane.

Amides of β-(3,5-di-tert-butyl-4-hydroxyphenyl) propionic acid: N,N'-bis(3,5-di-tert-butyl-4-hydroxyphenylpropionyl)hexamethylenediamine; N,N'-bis(3,5-di-tert-butyl-4-hydroxyphenylpropionyl) trimethylenediamine; N,N'-bis(3,5-di-tert-butyl-4-hydroxyphenylpropionyl)hydrazine.

Exemplary sterically hindered phenol antioxidant compounds include:

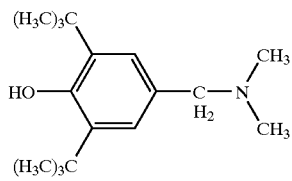

(II)

2,6-di-t-butyl-N,N-dimethylamino-p-cresol, which has a melting point of 94° C. (201° F.) and is a product of Albemarle Corporation of Richmond, Va., and available under the trade name Ethanox® 703 antioxidant;

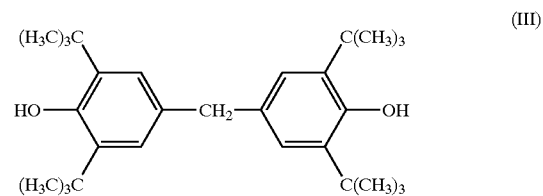

(III)

4,4'-methylenebis(2,6-di-t-butylphenol), which has a melting point of 154° C. (309° F.) and is a product of Albemarle Corporation of Richmond, Va., and available under the trade name Ethanox® 702 antioxidant;

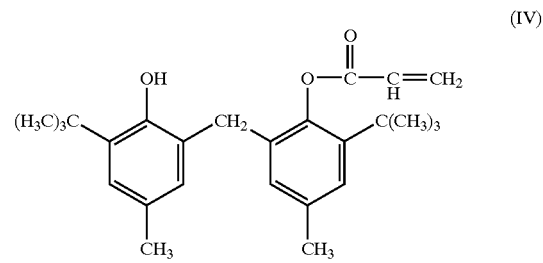

(IV)

2-tert-butyl-6-(3-tert-butyl-2-hydroxy-5-methylbenzyl)-4-methylphenyl acrylate, which has a melting point of 128–132° C. (262–270° F.) and is commercially available from Ciba Specialty Chemicals as Irganox 3052;

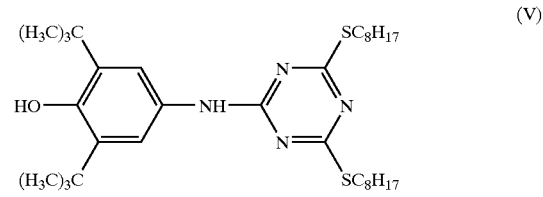

(V)

2,4-bis(n-octylthio)-6-(4-hydroxy-3,5-di-t-butylanilino)-1,3,5-triazine, which has a melting point of 390–407° C. (199–208.5° F.) and is a product of Ciba Special Chemicals of Tarrytown, N.Y., and available under the trade name Irganox 565;

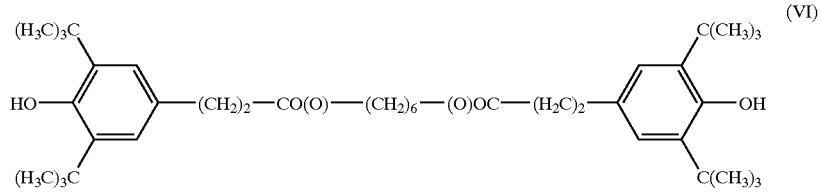

(VI)

1,6-hexanediyl 3,5-bis(1,1-di-methylethyl)-4-hydroxyphenylpropanoate, which has a melting point of 93–108° C. (199–227° F.) and is commercially available from Ciba Specialty Chemicals as Irganox 259;

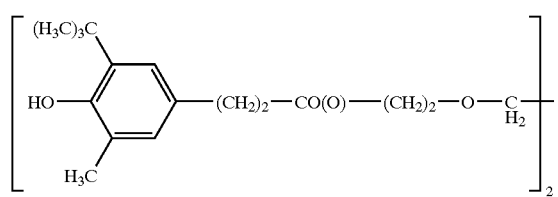
(VII)

1,2-ethanediylbis(oxy-2,1-ethanediyl)3-(1,1-dimethylethyl)-4-hydroxy-5-methyl-phenylpropanoate, which has a melting point of 76–79° C. (168–175° F.) and is commercially available from Ciba Specialty Chemicals as Irganox 245;

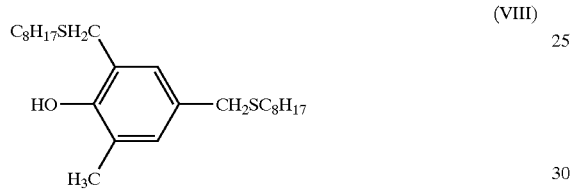
(VIII)

2-methyl-4,6-di[(octylthio)methyl]phenol, which is a liquid at ambient temperatures, and is commercially available from Ciba Specialty Chemicals as Irganox 1520;

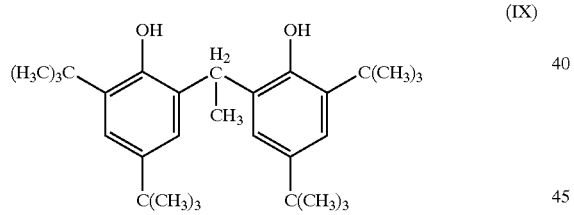
(IX)

2,2'-ethylidenebis(4,6-di-tert-butylphenol), which has a melting point of from about 161–163° C. (321–326° F.) and is commercially available from Ciba Specialty Chemicals as Irganox 129;

Preferred sterically hindered phenol antioxidants include:

A. Octadecyl 3,5-di-t-butyl-4-hydroxyhydrocinnamate having the structure:

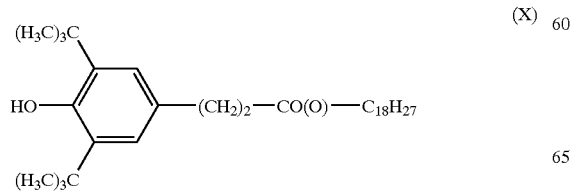
(X)

which has a melting point of 50–55° C. (122–131° F.) and is a product of Ciba Special Chemicals of Tarrytown, N.Y., and available under the name Irganox 1076;

B. Tetrakis[methylene(3,5-di-t-butyl-4-hydroxylhydrocinnamate)]methane having the structure:

C.

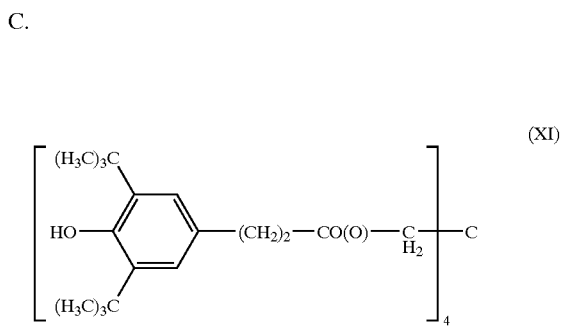
(XI)

which has a melting point of 110–125° C. (230–257° F.) and is a product of Great Lakes Chemical Corporation of West Lafayette, Ind., or Ciba Specialty Chemicals of Tarrytown, N.Y., and available under the trade name Anox 20 or Irganox 1010, respectively;

D. 1,3,5-tris-(3,5-di-t-butyl-4-hydroxybenzyl)isocyanurate having the structure:

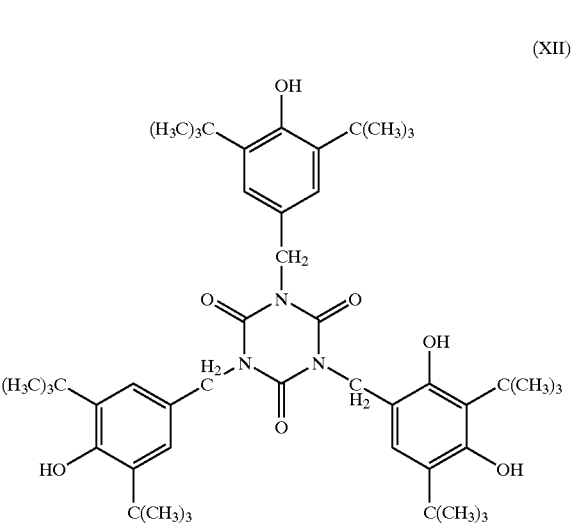
(XII)

which has a melting point of 218–224° C. (424.5–433.5° F.) and is a product of Albemarle Corporation of Richmond, Va., and available under the trade name Ethanox® 314 antioxidant or Ciba Specialty Chemicals of Tarrytown, N.Y., and available under the trade name Irganox 3114;

E. 1,3,5-tris-(4-t-butyl-3-hydroxy-2,6-dimethylbenzyl-1,3,5-triazine-2,4,6-(1H,3H,5H)-trione having the structure:

(XIV)

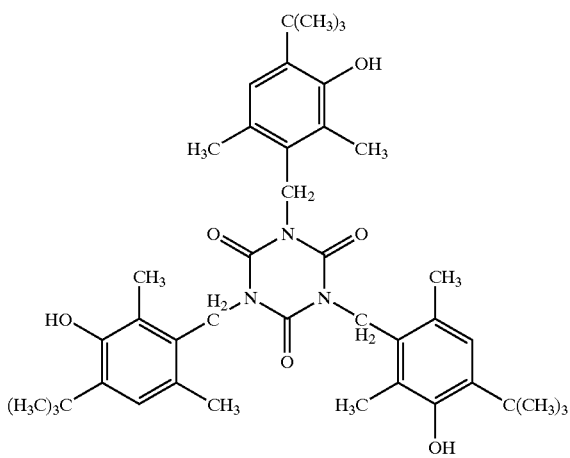

which has a melting point of 155–159° C. (311–318° F.) and is a product of Cytec of Stamford, Conn., and available under the trade name Cyanox 1790;

F. Thiodiethylenebis-(3,5-di-t-butyl-4-hydroxy) hydrocinnamate having the structure:

(XV)

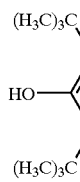(CH$_2$)$_2$CO(O)(CH$_2$)$_2$—S—(H$_2$C)$_2$(O)OC(H$_2$C)$_2$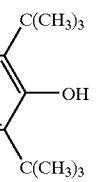

which is a product of Ciba Specialty Chemicals of Tarrytown, N.Y., which has a melting point of about 63° C. (145° F.), and is available under the trade name Irganox 1035; and, G. 1,3,5-trimethyl-2,4,6-tris-(3,5-di-tert-butyl-4-hydroxybenzyl)benzene having the structure:

(XVI)

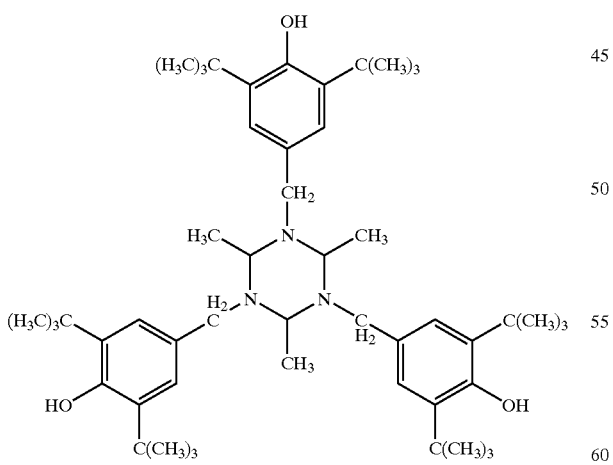

which has a melting point of 244° C. (471° F.) and is a product of Albemarle Corporation of Richmond, Va., and available under the trademark Ethanox®330 antioxidant.

Of these preferred sterically hindered phenol antioxidants, 1,3,5-trimethyl-2,4,6-tris(3,5-di-tert-butyl-4-hydroxybenzyl)benzene and 1,3,5-tris-(3,5-di-t-butyl-4-hydroxybenzyl)isocyanurate are most preferred.

In addition to the sterically hindered phenol antioxidant of the present invention, the stabilizer granules also may comprise a "secondary phosphite antioxidant," so designated because the phosphite antioxidant is always included with at least a "first" sterically hindered phenol antioxidant. Suitable secondary phosphite antioxidants are known in the art, and the proper type and amount of secondary phosphite antioxidant can be determined without undue experimentation by those of ordinary skill in the art. A suitable amount of secondary phosphite antioxidant will vary with the intended use of the additive system, typically from about 0 weight percent to about 80 weight percent, preferably from about 3 weight percent to about 70 weight percent. The weight ratio between the sterically hindered phenol antioxidant and the secondary phosphite antioxidant, where used, preferably ranges from about 20:1 to about 1:10, with a more preferred range of from about 10:1 to about 1:5, and a most preferred range of from about 2:1 to about 1:4.

Exemplary secondary phosphite antioxidants include, without limitation, such compounds as phosphites, phosphonites, fluoro-phosphonites and similar phosphite antioxidant compounds useful in stabilizing plastics. Examples include, but are not necessarily limited to organic phosphites and phosphonites, particularly in stabilizing polyolefin polymer compositions. These include aromatic phosphites and phosphonites, for example triphenyl phosphite, diphenyl alkyl phosphites, phenyl dialkyl phosphites, tris(diphenyl alkyl phosphite)amines, tris (nonylphenyl)phosphite, trilauryl phosphite, trioctadecyl phosphite, distearyl pentaerythrityl diphosphite, tris(2,4-di-tert-butylphenyl)phosphite, distearyl pentaerythrityl diphosphite, bis(2,4-di-tert-butylphenyl)pentaerythrityl diphosphite, tristearyl sorbityl triphosphite, tetrakis(2,4-di-tert-butylphenyl)-4,4'-biphenylene diphosphonite, 3,9-bis(2,4-di-tert-butyl-4-methylpheoxy)-2,4,8,10-tetraoxa-3,9-diphosphaspiro[5.5]undecane, 3,9-tris(2,4,6-tris-tert-butylphenoxy)-2,4,8,10-tetraoxa-3,9-diphosphaspiro[5,5] undecane and 2,2'-ethylidenebis(4,6-di-tert-butylphenyl) fluorophosphite.

Particularly useful phosphites include:

(XVII)

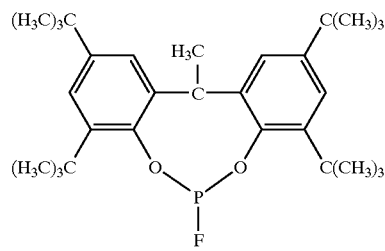

2,2-ethylidenebis-(4,6-di-t-butylphenyl)-fluorophosphonite, which has a melting point of 201° C. (393° F.) and is a product of Albemarle Corporation of Richmond, Va., and available under the trademark Ethanox®398 antioxidant;

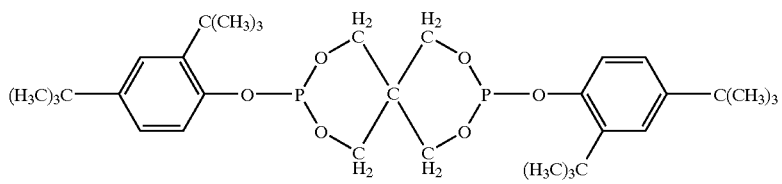

bis(2,4-di-t-butylphenyl)pentaerythritol-di-phosphite, which has a melting point of 160–175° C. (320–347° F.) and is a product of GE Specialty Chemicals of Parkersburg, W.Va., and available under the trade name Ultranox 626;

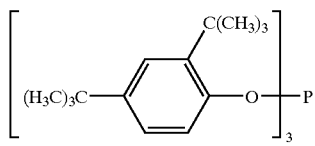

tris(2,4-di-tert-butylphenyl)phosphite, which has a melting point of 680–700° C. (360.5–370.5° F.) and is a product of Ciba Special Chemicals of Tarrytown, N.Y., and available under the trade name Irgafos 168;

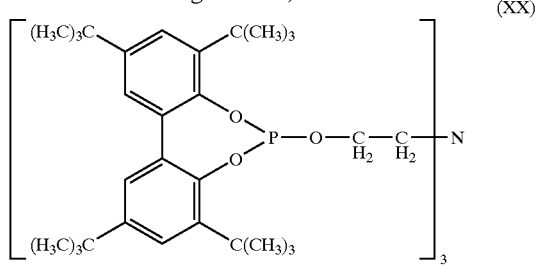

2,2',2"-nitrilo[triethyl-tris[3,3',5,5'-tetra-t-butyl-1,1'-biphenyl-2,2'-diyl]phosphite, which has a melting point of 200–754° C. (392–401° F.) and is a product of Ciba Special Chemicals of Tarrytown, N.Y., and available under the trade name Irgafos 12;

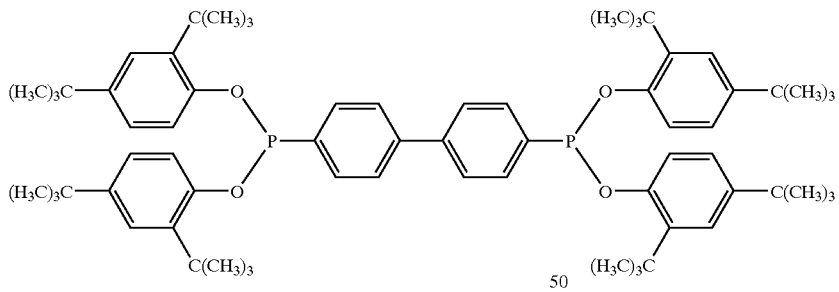

tetrakis (2,4-di-t-butylphenyl)-4,4'-biphenylenediphosphonite, which has a melting point of 85–95° C. (185–203° F.) and is a product of Clariant of Frankfurt, Germany, and available under the trade name Sandostab P-EPQ.

bis[2,4-dicumylphenyl]pentaerythritol diphosphite, which has a melting point of 225° C. (437° F.) or greater and is a product of Dover Chemical Corp., Dover Ohio, a subsidiary of ICC Industries, available under the name DOVERPHOS S-9228.

Preferred combinations of the sterically hindered phenol antioxidant and the secondary phosphite antioxidant include the combination of 1,3,5-trimethyl-2,4,6-tris-(3,5-di-tert-butylhydroxybenzyl)benzene and tris(2,4-di-tert-butylphenyl)phosphite.

The additive system of the present invention optionally may include one or more additive selected from the group consisting of plastic additives of metal soaps, antistatics, antiblocking agents, flame proofing agents, thioesters, internal lubricants, pigments, UV absorbers, light stabilizers, plasticizers, emulsifiers, optical brighteners, and/or blowing agents.

A preferred additive comprises acid neutralizers. Suitable acid neutralizers include, but are not necessarily limited to metal oxides, metal carbonates, hydrotalcites, and similar compounds useful in achieving acid neutralization in an additive system. The acid neutralizers may be naturally occurring minerals or synthetic compounds. Where used, an acid neutralizer typically comprises from about 0 weight percent to about 80 weight percent, preferably from about 20 weight percent to about 60 weight percent of the additive system. A preferred acid neutralizer comprises a hydrotalcite.

Suitable hydrotalcites for the present invention include those represented by the general formula:

$$M^{2+}_{1-x}M^{3+}_{x}(OH)_2(A^{n-})_{x/2}mH_2O$$

(XXI)

wherein $M^{2+}$ is selected from the group consisting of $Mg^{2+}$, $Ca^{2+}$, $Sr^{2+}$, $Ba^{2+}$, $Zn^{2+}$, $Cd^{2+}$, $Pb^{2+}$, $Sn^{2+}$, or $Ni^{2+}$; $M^{3+}=Al^{3+}$, $B^{3+}$ or $Bi^{3+}$; $A^{n-}$ is an anion having a valence of n, preferably selected from the group consisting of $OH^-$; $Cl^-$, $Br^-$; $I^-$, (XXII)

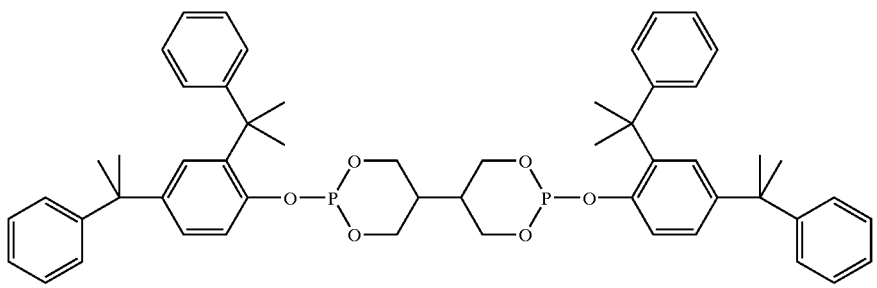

$ClO_4^-$, $HCO_3^-$, $CH_3COO^-$, $C_6H_5COO^-$, $CO_3^{2-}$, $SO_4^{2-}$; $(COO^-)_2$, $(CHOH)_4CH_2OHCOO^-$, $C_2H_4(COO)_2^{2-}$, $(CH_2COO)_2^{2-}$, $CH_3CHOHCO^-$, $SiO_3^{2-}$, $SiO_4^{4-}$, $Fe(CN)_6^{3-}$, $Fe(CN)_6^{4-}$ or $HPO_4^{2-}$; n is from about 1 to about 4; x is from about 0 to about 0.5; and m is from about 0 to about 2. Preferably, $M^{2+}$ is $Mg^{2+}$ or a solid solution of Mg and Zn, $M^{3+}$ is $Al^{3+}$; $A^{n-}$ is $CO_3^{2-}$, x is a number from 0 to 0.5, and m is a number from 0 to 2.

Exemplary hydrotalcites include, but are not necessarily limited to: $Al_2O_3 \cdot 6MgO \cdot CO_2 \cdot 12H_2O$; $Mg_{4.5}Al_2(OH)_{13} \cdot CO_3 \cdot 3{,}5H_2O$; $4MgO \cdot Al_2O_{0.3}CO_{0.2} \cdot 9H_2O$; $4MgO \cdot Al_2O_3 \cdot CO_2 6H_2O$; $ZnO \cdot 3MgO \cdot Al_2O_3 \cdot CO_2 \cdot 8-9H_2O$ and $ZnO \cdot 3MgO \cdot Al_2O_3 \cdot CO_2 \cdot 5-6H_2O$. The amount of hydrotalcite incorporated into the granules varies according to the intended use of the granules, and preferably is from about 0 weight percent to about 50 weight percent, more preferably from about 3 weight percent to about 40 weight percent hydrotalcite. Hydrotalcites are commercially available from Kyowa Chemical Company of Japan under the trademark DHT-4A, DHT-4C and DHT-4V. Preferred metal oxides include divalent metal oxides, particularly Group II metal oxides, most preferably zinc oxide and magnesium oxide. The amount of metal oxide used in the granules will vary with the intended use of the granules, preferably from about 0 weight percent to about 90 weight percent, more preferably from about 5 weight percent to about 60 weight percent, and most preferably from about 40 weight percent to about 50 weight percent.

Preferred metal carbonates include, but are not necessarily limited to divalent metal carbonates, preferably Group II metal oxides, most preferably calcium carbonate. The amount of metal carbonate used in the granules will vary with the intended use of the granules, preferably from about 0 weight percent to about 90 weight percent, more preferably from about 5 weight percent to about 60 weight percent.

Other suitable additives for use in the additive system include, but are not necessarily limited to Group II fatty acid metal salts (metal soaps) and similar compounds, such as magnesium, tin, zinc or preferably calcium salts having, for example, aliphatic saturated $C_2$–$C_{22}$ carboxylates, aliphatic olefinic $C_3$–$C_{22}$ carboxylates, aliphatic $C_2$–$C_{22}$ carboxylates substituted by at least one OH group, cyclic or bicyclic $C_5$–$C_{22}$ carboxylates, aromatic $C_7$–$C_{22}$ carboxylates, aromatic $C_7$–$C_{22}$ carboxylates substituted by at least one OH group, $C_1$–$C_{16}$ alkyl-substituted phenylcarboxylates and phenyl-$C_1$–$C_{16}$ alkylcarboxylates, preferably stearates, laurates and behenates. Other preferred metal soaps include, but are not necessarily limited to calcium stearate, zinc stearate, and magnesium stearate. The amount of metal soap used in the granules will vary with the intended use of the granules, preferably from about 0 weight percent to about 90 weight percent, and more preferably from about 5 weight percent to about 60 weight percent.

Preferred thioesters include, but are not necessarily limited to esters of β-thiodipropionic acid, for example the lauryl, stearyl, myristyl or tridecyl esters, mercaptobenzimidazole, the zinc salt of 2-mercaptobenzimidazole, zinc dibutyldithiocarbamate, dioctadecyl disulfide, pentaerythritol tetrakis(β-dodecylmercapto)propionate or ethylene glycol bismercaptoacetate. Suitable lubricants include, but are not necessarily limited to montan wax, fatty acid esters, polyethylene waxes, amide waxes, chlorinated paraffins, glycerol esters, alkaline earth metal soaps and other similar lubricants. Additives also may include UV absorbers and light stabilizers such as 2-(2'-hydroxyphenyl)benzotriazoles, for example 2-(2-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octophenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazol-2-yl phenol]; transesterification product of 2-[3'-tert-butyl-5'-(2-methoxycarbonylethyl)-2'-hydroxyphenyl]benzotriazole with polyethylene glycol 300; [R—$CH_2CH_2$—$COO(CH_2)_3$]$_2$ where R is 3'-tert-butyl-4'-hydroxy-5'-2H-benzotriazol-2-yl phenyl.

Hydroxybenzophenones, including but not necessarily limited to the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives. Esters of unsubstituted or substituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate. Acrylates, including but not necessarily limited to ethyl and isooctyl α-cyano-β,β-diphenylacrylate, methyl α-carbomethoxycinnamate, methyl and butyl-α-cyano-β-methyl-p-methoxycinnamate, methyl α-carbomethoxy-p-methoxycinnamate and N-(β-carbomethoxy-β-cyanovinyl)-2-methylindoline.

Nickel compounds, including but not necessarily limited to nickel complexes of 2,2'-thiobis[4-(1,1,3,3-tetraethylbutyl)phenol], such as the 1:1 and 1:2 complexes, if desired with additional ligands, such as n-butylamine, triethanolamine or N-cyclohexyldiethanolamine, nickel dibutyldithiocarbamate, nickel salts of monoalkyl esters, such as the methyl or ethyl esters, of 4-hydroxy-3,5-di-tert-butylbenzylphosphonic acid, nickel complexes of ketoximes, such as of 2-hydroxy-4-methylphenyl undecyl ketoxime, and nickel complexes of 1-phenyl-4-lauroyl-5-hydroxypyrazole, if desired with additional ligands.

Oxalamides, including but not necessarily limited to 4,4'-dioctyloxyoxanilide, 2,2'-diethoxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and mixtures thereof with 2-ethoxy-2'-ethyl-5,4'-di-tert-butyloxanilide, and mixtures of o- and p-methoxy- and of o- and p-ethoxy-disubstituted oxanilides.

2-(2-Hydroxyphenyl)-1,3,5-triazines, including but not necessarily limited to 2,4,6-tris(2-hydroxy-4-octyloxyphenyl)-1,3,5-triazine, 2-(2-hydroxy-4- octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyplhenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butoxypropoxy)phenyl]-4,6-bis(2,4-dimethylphenyl)-1,3,5-triazine, 2-[2-hydroxy-4-(2-hydroxy-3-octyloxypropoxy)phenyl]-4,6-bis(2,4-dimethylphenyl)-1,3,5-triazine.

Metal deactivators, including but not necessarily limited to N,N'-diphenyloxalamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalodihydrazide, oxanilide, isophthalodihydrazide, sebacobisphenyl hydrazide, N,N'-diacetyladipodihydrazide, N,N'-bissalicyloyloxalodihydrazide and N,N'-bissalicyloylthiopropionodihydrazide.

Peroxide scavengers, including but not necessarily limited to esters of β-thiodipropionic acid, for example the lauryl, stearyl, myristyl and tridecyl esters, mercaptobenzimidazole, the zinc salt of 2-mercaptobenzimidazole, zinc dibutyldithiocarbamate, dioctadecyl disulfide and pentaerythrityl tetrakis(β-dodecylmercapto)propionate.

Polyamide stabilizers, including but not necessarily limited to copper salts in combination with iodides and/or phosphorus compounds and salts of divalent manganese.

Basic costabilizers, including but not necessarily limited to melamine, polyvinylpyrrolidone, dicyandiamide, triallyl cyanurate, urea derivatives, hydrazine derivatives, amines, polyamides, polyurethanes, alkali and alkaline earth metal salts of higher fatty acids, for example zinc stearate, magnesium behenate, magnesium stearate, sodium ricinoleate, potassium palmitate, antimony pyrocatecholate and tin pyrocatecholate.

Nucleating agents, including but not necessarily limited to sodium salts of adipic acid, diphenylacetic acid, and benzoic acid. Clarifiers, including but not necessarily limited to 3,4-dimethylbenzylidine sorbital, which is a product of Milliken Chemical of Inman, S.C., and is available under the trade name Millad 3988.

Fillers and reinforcing agents, including but not necessarily limited to calcium carbonate, silicates, glass fibres, asbestos, talc, kaolin, mica, barium sulfate, metal oxides and hydroxides, carbon black and graphite.

Benzofuranones and indolinones, including but not necessarily limited to 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]-phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one and 3-(3,5-dimethyl-4-pivaloyloxyphenyl)-5,7-di-tert-butylbenzofuran-2-one.

The granules according to the present invention are suitable for the stabilization of organic polymers or plastics against thermal, oxidative or photoinduced degradation. Examples of such polymers include, but are not necessarily limited to polymers of monoolefins and diolefins, including, but not necessarily limited to polypropylene, polyisobutylene, polybut-1-ene, poly-4-methylpent-1-ene, polyisoprene or polybutadiene, as well as polymers of cycloolefins, for instance of cyclopentene or norbornene; furthermore polyethylene (which can be crosslinked), for example high density polyethylene (HDPE), low density polyethylene (LDPE), linear low density polyethylene (LLDPE) and branched low density polyethylene (BLDPE). Polyolefins, i.e., polymers of monoolefins, such as polyethylene and polypropylene, may be prepared by various processes, including: by means of free radicals (usually at high pressure and high temperature) or by means of a catalyst, where the catalyst usually contains one or more metals from group IVb, Vb, VIb or VIII. These metals usually contain one or more ligands, such as oxides, halides, alkoxides, esters, ethers, amines, alkyls, alkenyls and/or aryls, which can be either π or σ-coordinated. These metal complexes can be free or fixed to supports, for example to activated magnesium chloride, titanium(III) chloride, aluminum oxide or silicon oxide. These catalysts can be soluble or insoluble in the polymerization medium. The catalysts can be active as such in the polymerization or further activators can be used, for example metal alkyls, metal hydrides, metal alkyl halides, metal alkyl oxides or metal alkyl oxanes, where the metals are elements from groups Ia, IIa and/or IIIa. The activators can have been modified, for example, by means of further ester, ether, amine or silyl ether groups. These catalyst systems are usually known as Ziegler(-Natta), TNZ, metallocene or single site catalysts (SSC).

The granules of the present invention may further be used to process mixtures of the previously identified polymers, for example mixtures of polypropylene with polyisobutylene, polypropylene with polyethylene (for example PP/HDPE, PP/LDPE) and mixtures of different types of polyethylene (for example LDPE/HDPE). Additionally, the granules may be used with copolymers of monoolefins and diolefins with each other or with other vinyl monomers, for example ethylene-propylene copolymers, linear low density polyethylene (LLDPE) and its mixtures with low density polyethylene (LDPE), propylene-but-1-ene, propylene-isobutylene, ethylene-but-1-ene, ethylene-hexene, ethylene-methylpentene, ethylene-heptene, ethylene-octene, propylene-butadiene, isobutylene-isoprene, ethylene-alkyl acrylate, ethylene-alkyl methacrylate, ethylene-vinyl acetate copolymers or copolymers thereof with carbon monoxide or ethylene-acrylic acid copolymers and their salts (ionomers) and terpolymers of ethylene with propylene and a diene, such as hexadiene, dicyclopentadiene or ethylidenenorbornene; as well as mixtures of such copolymers and their mixtures with polymers previously identified, for example polypropylene-ethylene-propylene copolymers, LDPE-ethylene-vinyl acetate copolymers, LDPE-ethylene-acrylic acid copolymers, LLDPE-ethylene-vinyl acetate copolymers, LLDPE-ethylene-acrylic acid copolymers and polyalkylene-carbon monoxide copolymers with an alternating or random structure, and mixtures thereof with other polymers, for example polyamides. Other polymer systems such as hydrocarbon resins (for example $C_5$–$C_9$), including hydrogenated modifications thereof (for example tackifing resins) and mixtures of polyalkylenes and starch, polystyrene, poly(p-methylstyrene), poly(α-methylstyrene), and copolymers of styrene or α-methylstyrene with dienes or acrylic derivatives, for example styrene-butadiene, styrene-acrylonitrile, styrene-alkyl methacrylate, styrene-butadiene-alkyl acrylate, styrene-maleic anhydride, styrene-acrylonitrile-methyl acrylate; high impact strength mixtures of styrene copolymers and another polymer, for example a polyacrylate, a diene polymer or an ethylene-propylene-diene terpolymer; and block copolymers of styrene, for example styrene-butadiene-styrene, styreneisoprenestyrene, styrene-ethylene/butylene-styrene or styrene-ethylene/propylene-styrene may be processed with the granules of the present invention.

Graft copolymers of styrene or α-methylstyrene, for example styrene on polybutadiene, styrene on polybutadiene-styrene or polybutadiene acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or methacrylates on polybutadiene, styrene and acrylonitrile on ethylene-propylene-diene terpolymers, styrene and acrylonitrile on polyalkyl acrylates or polyalkyl methacrylates, styrene and acrylonitrile on acrylate-butadiene copolymers, as well as mixtures thereof with the copolymers of the previously identified styrene or α-methylstyrene with dienes or acrylic derivatives, for instance the copolymer mixtures known as ABS, MBS, ASA or AES polymers may be processed.

Other processed polymers include halogen-containing polymers, such as polychloroprene, chlorinated rubber, chlorinated or chlorosulfonated polyethylene, copolymers of ethylene and chlorinated ethylene, epichlorohydrin homo- and copolymers, in particular polymers from halogen-containing vinyl compounds, for example polyvinyl chloride, polyvinylidene chloride, polyvinyl fluoride, polyvinylidene fluoride, as well as copolymers thereof, for example vinyl chloride-vinylidene chloride, vinyl chloride-vinyl acetate or vinylidene chloride-vinyl acetate. Polymers derived from α,β-unsaturated acids and derivatives thereof, such as polyacrylates and polymethacrylates, polymethacrylates, polyacrylamides and polyacrylonitriles which have been impact modified by means of butyl acrylate. Copolymers of the monomers from α,β-unsaturated acids with each other or with other unsaturated monomers, for instance acrylonitrile-butadiene, acrylonitrile-alkyl acrylate, acrylonitrile-alkoxyalkyl acrylate or acrylonitrile-vinyl halide copolymers or acrylonitrile-alkyl methacrylate-butadiene terpolymers. Polymers derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; and their copolymers with olefins. Homopolymers and copolymers of cyclic ethers, such as polyalkylene glycols, polyethylene oxide, polypropylene oxide or copolymers thereof with bisglycidyl ethers. Polyacetals, such as polyoxymethylene and those polyoxymethylenes which contain comonomers, for example ethylene oxide; polyacetals modified with thermoplastic polyurethanes, acrylates or MBS. Polyphenylene oxides and sulfides, and mixtures thereof with styrene polymers or polyamides. Polyurethanes derived from polyethers, polyesters or polybutadienes with terminal hydroxyl groups on the one hand and aliphatic or aromatic polyisocyanates on the other, and precursors thereof. Polyamides and copolyamides derived from diamines and dicarboxylic acids and/or from aminocarboxylic acids or the corresponding lactams, such as nylon 4, nylon 6, nylon 6/6, 6/10, 6/9, 6/12, 4/6, and 12/12, nylon 11, nylon 12, aromatic polyamides obtained from m-xylene, diamine and adipic acid; polyamides prepared from hexamethylenediamine and isophthalic and/or terephthalic acid and optionally an elastomer as modifier, for example poly-2,4,4-trimethylhexamethylene terephthalamide or poly-m-phenylene isophthalamide. Block copolymers of the aforementioned polyamides with polyolefins, olefin copolymers, ionomers or chemically bonded or grafted elastomers; or with polyethers, for instance with polyethylene glycol, polypropylene glycol or polytetramethylene glycol. Further, EPDM- or ABS-modified polyamides or copolyamides; and polyamides condensed during processing ("RIM polyamide systems"). Polyureas, polyimides, polyamide-imides and polybenzimidazoles. Polyesters derived from dicarboxylic acids and diols and/or from hydroxycarboxylic acids or the corresponding lactones, such as polyethylene terephthalate, polybutylene terephthalate, poly-1,4-dimethylolcyclohexane terephthalate and polyhydroxybenoates as well as block polyether-esters derived from polyethers having hydroxyl end groups; also polycarbonate- or MBS-modified polymers. Polycarbonates, polyester carbonates, polysulfones, polyether sulfones and polyether ketones. Crosslinked polymers derived from aldehydes on the one hand and phenols, urea or melamine on the other, such as phenol-formaldehyde resins, urea-formaldehyde resins and melamine-formaldehyde resins. Drying and non-drying alkyd resins. Unsaturated polyester resins derived from copolyesters of saturated and unsaturated dicarboxylic acids with polyhydric alcohols, and vinyl compounds as crosslinking agents, and also halogen-containing modifications thereof of low inflammability. Crosslinkable acrylic resins, derived from substituted acrylic esters, for example epoxy acrylates, urethane acrylates or polyester acrylates. Alkyd resins, polyester resins or acrylate resins crosslinked with melamine resins, urea resins, polyisocyanates or epoxy resins. Crosslinked epoxy resins derived from polyepoxides, for example from bisglycidyl ethers or from cycloaliphatic diepoxides. Natural polymers, such as cellulose, natural rubber, gelatin and derivatives thereof which are chemically modified in a polymer-homologous manner, such as cellulose acetates, cellulose propionates and cellulose butyrates, or cellulose ethers, such as methylcellulose; and colophony resins and derivatives. Mixtures (polyblends) of polymers as mentioned above, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acylates, POM/thermoplastic PUR, PC/thermoplastic PUR, POM/acrylate, POM/MBS, PPO/HIPS, PPO/PA 6.6 and copolymers, PA/MDPE, PA/PP, PA/PPO. Natural and synthetic organic substances which are pure monomeric compounds or mixtures thereof, for example mineral oils, animal or vegetable fats, oils and waxes, or oils, waxes and fats based on synthetic esters (for example phthalates, adipates, phosphates or trimelliates), and blends of synthetic esters with mineral oils in any desired weight ratios, as used, for example, as spinning preparations, and aqueous emulsions thereof. Aqueous emulsions of natural or synthetic rubbers, for example natural rubber latex or latexes of carboxylated styrene-butadiene copolymers.

The granules of the present invention may additionally comprise one or more conventional plastic additives; preferably such additives are selected from the group consisting of sterically hindered amines (HALS), sterically hindered phenols, phosphites or phosphonites, hydrotalcites, metal oxides, metal carbonates, further metal soaps, antistatics, antiblocking agents, flameproofing agents, thioesters, internal lubricants, pigments, UV absorbers and further light stabilizers. The further plastics additive or additives may be in any convenient physical form, e.g., crystalline, powder, pellets, granules, dispersions or liquids. Preferred organic polymers are synthetic polymers and in particular the polymers from group 1, especially polyethylene and polypropylene. The granules are expediently added to the organic polymers to be stabilized in amounts of from 0.01 to 10%, preferably from 0.01 to 5%, based on the total weight of the organic polymer to be stabilized. The granules according to the invention and any further additives can be incorporated into the organic polymer by known methods, for example before or during molding or by applying the dissolved or dispersed granules to the polymer, if necessary with subsequent evaporation of the solvent. The granules can also be used for the production of so-called masterbatches. The method for the stabilization of an organic polymer comprising incorporating into said polymer an effective stabilizing amount, as described above, of the low-dust granules is another object of the instant invention. The preferred embodiments for the low-dust granules and the polymer apply analogously. The polymer stabilized in this way can be converted into a wide variety of forms in a conventional manner, for example into film, fibers, tapes, molding compositions or profiles.

Manufacture and testing of the stabilizer granules of the present invention may be accomplished as described in the following examples and procedures.

Balanced Hardness Test

The hardness test was designed to evaluate the formed pellets for the duel criteria of stabilizer handling conformity and favorable polymer processing characteristics. The hardness test included laying a single 3 mm diameter pellet of a given composition on a testing platform and then applying a compressive load across the pellet. The pellet was placed between two parallel non-cushioned steel plates with an increasing load applied to the top plate as a factor of time. The tested pellets generally produced a characteristic load verses time plot, with a maximum load reached at the point where the pellet begins to disintegrate into small particles. The maximum load divided by the length of the 3 mm diameter test pellet was the parameter used to measure hardness for a given pellet composition. It is believed that the hardness value increases linearly with the diameter of the pellet. The hardness test provided a toughness or crushing determination, with parameters in pounds per inch. Granule testing was typically accomplished over several replicate test specimens, such as about 10 to about 20 test specimens, with the averaging of the results. The resulting graph of the averaged tests, as seen in FIG. 1, has the x-axis as either time or crosshead displacement, as the crosshead is moving at a constant rate providing either time (minutes) or displacement (millimeters). A typical and convenient rate for the crosshead movement is 0.02 in/min. FIG. 1 illustrates a load versus time plot for the pellets processed from Ethanox® antioxidant with mixed isopropanol at 1 part by weight and cyclohexane at 3 parts by weight, using 9 parts by weight processing agent and 100 part by weight Ethanox® 330 antioxidant.

Pelletization of the Sterically Hindered Phenol Antioxidant

The organic processing agents are combined with the first antioxidant so that at least 1 gram of the first antioxidant is dispersed in every 100 mL of processing agent. The antioxidant may be proportionally added to the selected processing agent, or the organic processing agent may be added to the antioxidant powder. The resulting solution is brought in situ into contact with the remaining antioxidant powder so as to effect the formation of a paste of the antioxidant which is suitable for pelletization. The concentration of the organic processing agent, i.e., selected solvent plus alcohol, required to form the paste which is suitable for pelletization generally ranges from about 3 parts by weight organic processing agent per 97 parts by weight of additive powder, i.e., sterically hindered phenol antioxidant plus optionally secondary phosphite antioxidant and acid neutralizer, to about 20 parts by weight of organic processing agent per 80 parts by weight of additive powder. Generally, the organic processing agent provides from about 20 weight percent to about 50 weight percent of an alcohol. Cylindrical pellets were formed in a die press.

PELLET EXAMPLE 1

Ethanox 330® Antioxidant Pellets Formed with Cyclohexane

Cylindrical pellets of 1,3,5-trimethyl-2,4,6-tris-(3,5-di-tert-butyl-4-hydroxybenzyl)benzene powder (Ethanox® 330 Antioxidant) were prepared by combining 20 lb of Ethanox® 330 powder with 2.4 lb cyclohexane solvent and tumble blended for 5 minutes to obtain a homogeneous mixture. The homogeneous mixture was fed, at 55–60 lb/hr rate, to a Kahl Model 14-175 Pellet Press equipped with a die plate containing holes of 3 mm diameter and 10.5 mm pressway length and operating at a rotor speed of nominally 100 rpm. The output product of the pellet mill was dried for 60 minutes in a forced-air oven operating under nitrogen atmosphere and a temperature of 100° C., after which the dried product dry sieved with a US Standard No. 12 screen to remove the fines (minus 12 mesh powder). The Ethanox® 330 particles thus obtained were cylindrical pellets of 3 mm diameter with a hardness of 18 lb/in.

PELLET EXAMPLE 2

Ethanox 330® Antioxidant Pellets Formed with Mixed Cyclohexane/Isopropanol Organic Processing Agent The procedures of Example 1 were repeated, except the processing solvent used to prepare the feed mixture consisted of 1.8 lb of cyclohexane and 0.6 lb of isopropanol. The Ethanox® 330 particles thus obtained were cylindrical pellets of 3 mm diameter with a hardness of 15 lb/in.

COMPARATIVE PELLET EXAMPLE 1

4000 grams of 1,3,5-trimethyl-2,4,6-tris-(3,5-di-tert-butyl-4-hydroxybenzyl)benzene powder, with no organic processing agent added, was fed into a Kahl Model 14-175 Pellet Mill operating at 100 rpm rotor speed and equipped with a die plate having holes of 2 mm diameter and 6 mm pressway length. The product from the pellet mill consisted of nearly all fine powder with a small proportion of very soft pellets.

PELLET EXAMPLE 3

Irganox 3114 Antioxidant Pellets Formed with Cyclohexane Processing Solvent

Cylindrical pellets of 1,3,5-Tris-(3,5-di-t-butyl-4-hydroxybenzyl)isocyanurate powder (Irganox 3114 obtained tom Ciba Specialty Chemicals) were prepared by combining 20 lb of Irganox 3114 powder and 2 lb of cyclohexane solvent and tumble blending for 5 minutes to obtain a homogeneous feed mixture. The homogeneous mixture was fed, at nominally 85 lb/hr rate, to a Kahl Model 14-175 Pellet Press equipped with a die plate containing holes of 3 mm diameter and 10.5 mm pressway length and operating at a rotor speed of nominally 100 rpm. The output product of the pellet mill was dried for 70 minutes in a forced-air oven operating under nitrogen atmosphere and a temperature of 100° C. The dried product was dry sieved with a US Standard No. 8 screen to remove the fines (minus 8 mesh powder). The Irganox 3114 particles thus obtained were cylindrical pellets of 3 mm diameter with a hardness of 22 lb/in.

PELLET EXAMPLE 4

Irganox 3114/ Secondary Phosphite Blend Pellets Formed with Mixed Cyclohexane/Isopropanol Processing Solvent Cylindrical pellets having a blend of 1,3,5-Tris-(3,5-di-t-butyl-4-hydroxybenzyl)isocyanurate hindered phenol antioxidant (Irganox 3114 obtained from Ciba Specialty Chemicals) with tris(2,4-di-t-butylphenyl)phosphite secondary antioxidant (Irgafos 168 obtained from Ciba Specialty Chemicals) in 1:1 proportions by weight were prepared by combining 10 lb each of Irganox 3114 and Irgafos 168 powders and tumble blending the mixture for 5 minutes. 1.2 lb of cyclohexane and 1.2 lb of isopropanol were added and the mixture was tumble blended for an additional 5 minutes to obtain a homogeneous feed mixture. The homogeneous feed mixture was fed, at nominally 75 lb/hr rate, to a Kahl Model 14-175 Pellet Mill equipped with a die plate with holes of 3 mm diameter and 10.5 mm pressway length. The output of the pellet mill was dried for 65 minutes in a forced air oven operating under nitrogen atmosphere at a temperature of 100° C. The dry product was then dry sieved with a US Standard No. 8 screen to remove the fines (minus 8 mesh material). The finished particles thus obtained were cylindrical pellets having a diameter of nominally 3 mm and a hardness of 20 lb/in.

PELLET EXAMPLE 5

Ethanox® 330 Antioxidant/Secondary Phosphite Antioxidant Blend Pellets Formed with Methylethylketone Processing Solvent Cylindrical pellets having a blend of Ethanox® 330 Antioxidant with tris(2,4-di-t-butylphenyl) secondary phosphite antioxidant (Irgafos 168 obtained from Ciba Specialty Chemicals) in 1:2 proportions by weight were prepared by combining 13.3 lb of Irgafos 168 powder and 6.7 lb of Ethanox® 330 Antioxidant powder and tumble blending for 5 minutes. 1.5 lb of methylethylketone solvent were added to the blended powders which was then tumble blended for 5 minutes to obtain a homogeneous feed mixture. The homogeneous feed mixture was fed, at nominally 65–70 lb/hr rate, to a Kahl Model 14-175 Pellet Mill equipped with a die plate with holes of 3 mm diameter and 9 mm pressway length. The output of the pellet mill was dried for about 2 hours in a forced air oven operating under nitrogen atmosphere at a temperature of 105° C. The dried product was dry sieved with a US Standard No. 8 screen to remove the fines (minus 8 mesh material). The finished particles thus obtained were cylindrical pellets having a diameter of nominally 3 mm and a hardness of 14 lb/in.

PELLET EXAMPLE 6

Ethanox® 330 Antioxidant/Secondary Phosphite Antioxidant Blend Pellets Formed with Mixed Methylethylketone/Acetone Example 5 was repeated using as an organic processing agent 1.0 lb of methylethylketone and 0.5 lb. of acetone, and with the feeding rate to the pellet mill at nominally 55 lb/hr. The finished particles obtained were cylindrical pellets having a diameter of nominally 3 mm and a hardness of 14 lb/in.

PELLET EXAMPLE 7

Ethanox® 330 Antioxidant/Acid Neutralizer Blend Pellets Formed with Methylethylketone Solvent Cylindrical pellets having a blend of Ethanox® 330 Antioxidant with calcium stearate acid neutralizer in 60:40 proportion by weight were prepared by combining 4.8 lb of Ethanox® 330 Antioxidant powder with 3.2 lb of calcium stearate powder (Synpro 114-40 calcium stearate obtained from Ferro Corporation of Walton Hills, Ohio) and tumble blending the powders for 3 minutes. 0.6 lb of methylethylketone were added and the mixture was tumble blended for 3 minutes to obtain a homogeneous feed mixture. The homogeneous feed mixture was fed, at a rate of nominally 40 lb/hr, to a Kahl Model 14-175 pellet mill equipped with a die plate having holes of 3 mm diameter and 12 mm pressway length. The output of the pellet mill was dried for about one hour in a forced air oven operating under nitrogen atmosphere and at a temperature of 90° C. and then dry sieved with a US Standard No. 12 screen to remove the fines (minus 12 mesh particles). The finished particles thus obtained were cylindrical pellets having a diameter of nominally 3 mm and a hardness of 24 lb/in.

PELLET EXAMPLE 8

Pellets of Ethanox® 330 Antioxidant/Secondary Phosphite Antioxidant/Acid Neutralizer Blend Pellets having a blend of Ethanox® 330 Antioxidant powder with a secondary phosphite antioxidant powder (Irgafos 168 Antioxidant obtained from Ciba Specialty Chemicals) and two acid neutralizers (DHT-4A obtained from Kyowa Chemical Industry Co., LTD, and Hydense 5862 calcium stearate powder obtained from Baerlocher USA). Three different processing agents were used combined with 5.96 lb of Ethanox® 330 powder, 8.6 lb of Irgafos 168 powder, 4.64 lb of DHT-4A powder, and 0.8 lb of calcium stearate powder in a tumble blender and blending for 5 minutes. 2.0 lb of the processing agent was added and tumble blending was done for 5 minutes to obtain a homogenous feed mixture. The homogeneous feed mixture was fed, at about 40–50 lb/hr rate, to a Kahl Model 14-175 Pellet Mill equipped with a die plate having holes of 3 mm diameter and 10.5 mm pressway length. The product was then dried for about 70 minutes in a forced air oven operating in nitrogen atmosphere and at a temperature of 100° C. The dried product was dry sieved with a US Standard No. 12 screen to remove the fines (minus 12 mesh particles). The three pellet samples were prepared with the following processing agents: Sample A) isopropanol; Sample B) mixture of isopropanol and methylethylketone in 25:75 proportions by weight; and Sample C) methylethylketone. The finished particles of Samples A, B, and C thus obtained in this manner were cylindrical pellets of nominally 3 mm diameter having hardnesses of 12, 16, and 20 lb/in., respectively.

Hosokawa Flowability of Antioxidant Blend Pellets

Hosokawa Flowability of the following blends was tested using known procedures, namely:

1) Measuring five standard powder properties, namely aerated bulk density, packed bulk density, angle of repose, angle of spatula, and particle uniformity (from sieve size analyses);

2) From the aerated and packed bulk densities, calculating a factor called the compressibility;

3) From correlation charts, assigning an index rating (0–25 scale) to the angle of repose, the angle of spatula, the particle uniformity, and the compressibility; and 4) Summing the four index ratings of Step 3 to arrive at the numerical value of the Hosokawa Flowability.

The following were the results:

| Blend Composition* | Processing Solvent** | Hosokawa Flowability |
|---|---|---|
| 100% E-330 | 9.0 MEK + 3 IPA | 83 |
| 50% E-330/ 50% I-168 | 10.0 MEK | 78 |
| 33% E-330/ 67% I-168 | 10.0 MEK | 83 |
| 50% E-314/ 50% I-168 | 6.0 CHX + 6.0 IPA | 82 |
| 100% E-330 Powder | Not Pelletized | 44 |
| 100% E-314 | 9.0 cyclohexane + 3.0 IPA | 85 |
| 33.3% E-314 67% I-168 | 6.0 cyclohexane + 6.0 IPA | 85 |

Formation of Agglomerates of Sterically Hindered Phenol Additive System

In the examples that follow, all portions of material is given in parts by weight. Unless noted otherwise, the agglomeration process was performed by: 1) adding the indicated proportions of the processing aid liquid and the additive powder to a glass Erlenmeyer flask; 2) admixing the materials of Step (1) with a spatula until a paste-like slurry formed; 3) rotating the flask at about 60 rpm with a rotoevaporator head while simultaneously tapping the flack gently with the fingers (to stimulate the tumbling action of a drum or pin agglomerator apparatus) to affect the agglomeration into spherical particles; 4) transferring the agglomerated particles to a petri dish for drying in a forced-air oven at the indicated temperature. In those cases where the "additive powder" of Step (1) comprised a mixture of two or more powder components, the powder mixture was dry blended prior to adding the processing aid liquid.

In the examples, processability testing or agglomerate hardness measurements to determine the processability characteristics of the agglomerates, i.e. hardness and attrition resistance was determined by subjecting the agglomerates to manual manipulation so as to observe the friability of the agglomerate.

Formation of Agglomerates

AGGLOMERATE EXAMPLE I

Agglomeration of ETHANOX® 330/Hydrotalcite Additive System 1 part of hydrotalcite powder (commercially available from Kyowa Chemical Company under the trademark DHT-4V) and 2 parts of 1,3,5-trimethyll-2,4,6-tris-(3,5-di-tert-butyl-4-hydroxylbenzyl benzene), commercially available from Albemarle Corporation under the trademark ETHANOX® 330, were dry blended to form the desired additive system powder composition. This additive system powder was agglomerated using 0.79 parts methanol processing aid per 5 parts of powder. The resulting agglomerate was dried at 85° C. The dried agglomerate was dry sieved with a U.S. Standard No. 8, 19 screen to remove the fine particles (−18 mesh) and to obtain the desired additive system agglomerate particles in 80% yield. The resulting product consisted of essentially spherical particles ranging in a size from about 1 mm to about 4 mm in diameter. The resulting product of agglomerated particles were subject to manual characterization and judged to have very good hardness and therefore good resistance to particle attrition during conveying operations.

AGGLOMERATE EXAMPLE II

Agglomeration of ETHANOX® 330/Hydrotalcite/ Secondary Phosphite Additive System 42 parts ETHANOX® 330 Antioxidant, 52 parts of a commercially available secondary phosphite antioxidant, available from Ciba Specialty Chemicals under the trademark IRGAFOS 168, and 16 parts of DHT-4V hydrotalcite were dry blended to form the desired additive system powder composition. The additive system was agglomerated using 0.79 parts of denatured ethanol process aid per 6 parts of additive system powder composition. The resulting agglomerated particles were subjected to drying at 83° C. The resulting dried agglomerate product particles were dry sieved with a U.S. Standard No. 18 screen to give 77% yield of essentially spherical particles ranging in diameter from about 1 to about 5 mm. Manual characterization of the particles indicated very good hardness and therefore good resistance to particle attrition during conveying operations.

AGGLOMERATE EXAMPLE III

Agglomeration of ETHANOX® 330/Zinc Oxide/ Secondary Phosphite Additive System

Example II was essentially repeated but with 44 parts of ETHANOX® 330 Antioxidant, 38 parts of IRGAFOS 168, and 18 parts of ZnO (Grade Az066L obtained from Midwest Zinc Company) as the desired additive system powder composition. Manual characterization of the dried agglomerate particles indicated very good particle hardness and therefore good resistance to particle attrition during conveying operations.

AGGLOMERATE EXAMPLE IV

Agglomeration of IRGANOX 1010/Hydrotalcite/ Secondary Phosphite Additive System 5.3 parts of pentaerythritol ester of β-(3,5-di-tert-butyl-4-hydroxyphenyl)propionic acid, a commercially available hindered phenolic antioxidant obtainable from Ciba Specialty Chemicals under the trademark IRGANOX 1010, 1.59 parts of DHT-4V acid neutralizer, and 2.61 parts of IRGAFOS 168 were dry blended to obtain the desired additive system powder composition. Agglomeration of this additive system powder blend was affected using 1.1 parts of isopropanol as the processing aid per 9.5 parts of powder blend. The resulting agglomerate particles were dried at 85° C. The resulting dried agglomerates were to essentially spherical of nominally 1–5 mm diameter and having very good hardness.

AGGLOMERATE EXAMPLE V

Agglomeration with Acetone/Methanol 1 part of DHT-4V hydrotalcite and 2 parts ETHANOX® 330 antioxidant were dry blended to form an additive system powder mix. The additive powder blend was agglomerated using a processing aid liquid, 0.79 parts of a 50:50 mixture of acetone and methanol having 5 grams of ETHANOX® 330 Antioxidant per 100 mL cosolvent processing aid dissolved therein. The resulting agglomerate was dried at 85° C. The resulting agglomerate particles were then dry sieved with a U.S. Standard No. 18 screen to remove the fine particles and to obtain the desired additive system agglomerate particles in 80% yield. The resulting agglomerate particles were essentially spherical and ranged in size from about 1 mm to about 5 mm in diameter. Using manual manipulation the particles were judged to have a very good hardness. Moreover, the agglomerated particles obtained with the processing aid containing acetone cosolvent were considerably harder than the agglomerate of Example I.

AGGLOMERATE EXAMPLE VI

Agglomeration with Acetone/Ethanol 1 part of DHT-4V hydrotalcite and 2 parts ETHANOX® 330 antioxidant were dry blended to form an additive system powder mix. This additive powder blend was agglomerated using as a processing aid liquid, 0.79 parts of a 50:50 mixture of acetone and denatured ethanol having 5 grams of ETHANOX® 330 Antioxidant per 100 mL cosolvent processing aid dissolved therein. The resulting agglomerate was dried at 85° C. The resulting agglomerate particles were then dry sieved with a U.S. Standard No. 18 screen sieve to remove the fine particles and to obtain the desired additive system agglomerate particles in 80% yield. The resulting agglomerated particles were essentially spherical and ranged in size from about 1 mm to about 5 mm in diameter. Using manual manipulation, the particles were judged to have a very good hardness. Moreover, the agglomerated particles obtained with the processing aid containing acetone cosolvent were considerably harder than the agglomerates of Example 1.

AGGLOMERATE EXAMPLE VII

Agglomeration with Acetone/Methanol 1 part of DHT-4V hydrotalcite and 2 parts of ETHANOX® 330 antioxidant were dry blended to form an additive system powder mix. This additive powder blend was agglomerated using as a processing aid liquid, 0.79 parts of a 30:70 mixture of acetone and methanol having 5 grams of ETHANOX® 330 Antioxidant per 100 mL cosolvent processing aid dissolved therein. The resulting agglomerate was dried at 85° C. The resulting agglomerate particles were dry sieved with a U.S. Standard No. 18 screen to remove the fine particles and to obtain the desired additive system agglomerate particles in 80% yield. The resulting agglomerated particles were essentially spherical and ranged in size from about 1 mm to about 5 mm in diameter. Using manual manipulation, the particles were judged to have a hardness which was intermediate to that of the corresponding particles of Examples 1 and IV.

AGGLOMERATE EXAMPLE VIII

Agglomeration with Acetone/Ethanol 1 part of DHT-4V hydrotalcite and 2 parts ETHANOX® 330 antioxidant were dry blended to form an additive system powder mix. This additive powder blend was agglomerated using as a processing aid liquid, 0.79 pats of a 30:70 mixture of acetone and denatured ethanol having 5 grams of ETHANOX® 330 Antioxidant per 100 mL cosolvent processing aid dissolved therein. The resulting agglomerate was dried at 85° C. The resulting particles were then dry sieved with U.S. Standard No. 18 screen to remove the fine particles and to obtain the desired system agglomerate particles in 80% yield. The resulting agglomerated particles were essentially spherical and ranged in size from about 1 mm to about 5 mm in diameter. Using manual manipulation, the particles were judged to have a hardness which was intermediate to that of the corresponding particles of Examples I and V.

Agglomerate Examples V–VIII illustrate that the introduction of solvent and dissolved phenolic antioxidant into the processing aid produced an increase in the hardness of the agglomerate particles. In addition, Agglomerate Examples VII and VIII illustrate that the hardness of the agglomerate particles is controlled by the relative proportion of the solvent and the hardness varied inversely with the relative proportion of the alcohol.

The specific examples herein disclosed are to be considered as being primarily illustrative. Various changes beyond those described will occur to those skilled in the art and such changes are to be understood as forming a part of this invention as they fall within the spirit and scope of the appended claims.

AGGLOMERATE EXAMPLE IX

Agglomeration with Toluene/Ethanol

The processing aid liquid (A) was prepared by admixing ETHANOX® 330 antioxidant powder (10 parts), toluene (47.2 parts), denatured ethanol (42.8 parts). The agglomeration process was performed on 1 part (A) admixed with 5 parts of additional ETHANOX® 330 antioxidant powder. The result agglomerated particles were dried for about 20 minutes in the oven beginning at about 70° C. and gradually increasing the temperature to about 115° C. The dried agglomerate consisted of essentially spherical particles ranging from 1 mm to 4 mm in diameter. The resulting dried agglomerate particles were subjected to manual characterization and judged to have very good hardness and therefore good resistance to particle attrition during conveying operations.

For comparative purposes, the ETHANOX® 330 antioxidant powder was agglomerated under the same conditions as above described but with two different processing aid liquids (B) and (C). Processing aid liquid (B) was a saturated solution of ETHANOX® 330 antioxidant dissolved in denatured ethanol, and processing aid liquid (C) consisted of 10 parts of ETHANOX® 330 antioxidant dissolved in toluene. With (B), the wet agglomerated spherical particles that formed mostly disintegrated into fine powder during the drying operation, and the few dried spherical particles that remained were extremely soft and exhibited very low abrasion resistance. With (C), the tumbling action of the agglomeration apparatus failed to produce the desired spherical particles, leaving an essentially continuous slurry mass instead. This comparative example illustrates that the processing liquid aid of the instant invention is necessary both to form the desired spherical agglomerated particles and to impart the desired hardness to the dried agglomerated particles.

AGGLOMERATE EXAMPLE X

Agglomeration with Phosphite Antioxidant

The agglomeration process with agglomeration aid of (A) Example IX essentially was repeated but with the powder component replaced with a blend consisting of ETHANOX® 330 antioxidant powder (1 part) and IRGAFOS 168 phosphite powder (1 part) (tris-(2,4-di-tert-butylphenyl) phosphite), (a commercial secondary phosphite antioxidant product obtained from Ciba Specialty Chemicals). The dried agglomerate particles thus obtained essentially were spherical in shape, were nominally 1 to 4 mm in diameter, an when subjected to manual manipulation were judged to have very good hardness and therefore good resistance to particle attrition during conveying operations.

AGGLOMERATION EXAMPLE XI

Agglomeration with IRGANOX 1010 Blend with Secondary Phosphite

The process aid liquid (D) was prepared by admixing IRGANOX 1010 antioxidant powder (pentaerythrityl ester of β-(3,5-di-tert-butyl-4-hydroxyphenyl)propionic acid) (6 parts) (a commercial hindered phenolic antioxidant obtained from Ciba Specialty Chemicals), acetone (47 parts), and methanol (47 parts). Processing aid liquid (E) was prepared by admixing IRGANOX 1010 (6 parts), acetone (70.5 parts), and methanol (23.5 parts). A powder blend consisting of equal parts by weight of IRGANOX 1010 and IRGAFOS 168 also was prepared. The agglomeration of the powder blend was affected by utilizing 0.55 parts of agglomeration aid liquid with 5 parts of blended powder followed by drying in the oven at 71° C. for 30 minutes. The dried agglomerate particles thus obtained using processing aid liquids (D) and (E) essentially were spherical in shape, were nominally 1 to 4 mm in diameter, and when subjected to manual manipulation were judged to have very good hardness and therefore good resistance to particle attrition during conveying operations. Moreover, the agglomerate particles made with processing aid (E) were considerably harder than those made with processing aid (D), thereby demonstrating that the hardness of the agglomerated particles is increased as the proportion of alcohol in the agglomeration aid liquid is decreased.

AGGLOMERATE EXAMPLE XII

Agglomeration with Acetone/Methanol

The processing aid liquid (F) was prepared in the same manner as the processing aid liquid (D) of Example XI except ETHANOX® 330 antioxidant powder was substituted for the IRGANOX 1010 antioxidant powder. ETHANOX® 330 antioxidant powder was agglomerated with processing aid liquid (F) and subsequently dried by repeating the procedures utilized in Example XI. The dried agglomerate particles of ETHANOX® 330 antioxidant thus obtained were essentially spherical in shape, were nominally 1 to 5 mm in diameter, and when subjected to manual manipulation were judged to have very good hardness and therefore good resistance to particle attrition during conveying operations.

What is claimed is:

1. A process for manufacturing dried granules that are at least in the form of agglomerates or pellets, said process comprising:

mixing an organic processing agent comprising an amount of a friability reduction agent with a powder comprising an additive system comprising at least a first sterically hindered phenol antioxidant under conditions that are effective to form a wet paste;

processing said wet paste to form wet granules in the form of wet agglomerates or wet pellets without melting said sterically hindered phenol antioxidant; and, exposing said wet granules to conditions that are effective to remove said organic processing agent from said wet granules but ineffective to melt said sterically hindered phenol antioxidant, thereby producing said dried granules.

2. The process of claim 1, wherein said friability reduction agent is an alcohol.

3. The process of claim 1 further comprising controlling balanced hardness of said dried granules by adjusting said amount of said friability reduction agent.

4. The process of claim 3, wherein said friability reduction agent is an alcohol.

5. The process of claim 4, wherein said alcohol comprises a composition of the formula ROH wherein R is an alkyl group of from 1 to 8 carbon atoms.

6. The process of claim 4, wherein said alcohol is selected from the group consisting of methanol, ethanol, and 2-propanol.

7. A process for manufacturing dried granules that are at least in the form of agglomerates or pellets, said granules made by a process comprising:

A) mixing (i) an organic processing agent comprising (a) a friability reduction agent and (b) an organic solvent with (ii) a powder comprising an additive system comprised of at least a first sterically hindered phenol antioxidant, under conditions that are effective to form a wet paste;

B) processing said wet paste into at least wet agglomerates or wet pellets without melting any solid component(s) in the agglomerates or pellets; and C) exposing said agglomerates or pellets to conditions that are effective to remove said organic processing agent from said agglomerates or pellets and to dry said agglomerates or pellets but ineffective to melt any solid component of the agglomerates or pellets, to thereby produce dried granules in the form of dried agglomerates or dried pellets.

8. The process of claim 7 wherein the processing of said paste in B) is performed by agglomerating said paste with agglomerating equipment.

9. The process of claim 8 wherein the agglomerating is conducted using a paste in which at least about 20 weight percent of the organic processing agent is said friability reduction agent.

10. The process of claim 9 wherein up to about 80 weight percent of the organic processing agent is an organic solvent capable of dissolving at least about 2 g of sterically hindered phenol per 100 mL of such solvent.

11. The process of claim 8 wherein the agglomerating of the paste is performed in a pin agglomerator.

12. The process of claim 11 wherein the agglomerating is conducted using a paste in which at least about 20 weight percent of the organic processing agent is said friability reduction agent.

13. The process of claim 12 wherein up to about 80 weight percent of the organic processing agent is an organic solvent capable of dissolving at least about 2 g of sterically hindered phenol per 100 mL of such solvent.

14. The process of claim 7 wherein the processing of said paste in B) is performed by pelletizing said paste.

15. The process of claim 14 wherein the pelletizing is conducted using a paste in which the organic processing agent is at least one organic solvent capable of dissolving at least about 2 g of sterically hindered phenol per 100 mL of such solvent.

16. The process of claim 14 wherein the pelletizing is conducted using a paste in which the organic processing agent is a mixture of at least one friability reduction agent and at least one organic solvent capable of dissolving at least about 2 g of sterically hindered phenol per 100 mL of such solvent.

17. The process of any of claims 14 or 15–16 wherein the pelletizing is conducted using a pellet press equipped with a die plate.

18. The process of any of claims 7–14 or 15–16 wherein said organic processing agent and said powder are mixed in proportions in the range of (a) about 3 parts by weight of processing agent to about 97 parts by weight of powder, to (b) about 20 parts by weight of processing agent to about 80 parts by weight of powder.

19. The process of any of claims 7–14 or 16 wherein said friability reduction agent comprises methanol, ethanol, or 2-propanol.

20. The process of any of claims 7–14, 16 or 17 wherein said solvent consists essentially of solvent selected from the group consisting of methylene chloride, chloroform, toluene, acetone, methyl ethyl ketone, xylene, cyclohexane, methylcyclohexane, hexane, and combinations thereof.

* * * * *

UNITED STATES PATENT AND TRADEMARK OFFICE
CERTIFICATE OF CORRECTION

PATENT NO. : 6,800,228 B1  Page 1 of 1
APPLICATION NO. : 09/528675
DATED : October 5, 2004
INVENTOR(S) : John Semen It is certified that error appears in the above-identified patent and that said Letters Patent is hereby corrected as shown below:

Column 11, the structure on lines 60-67 is shown as:

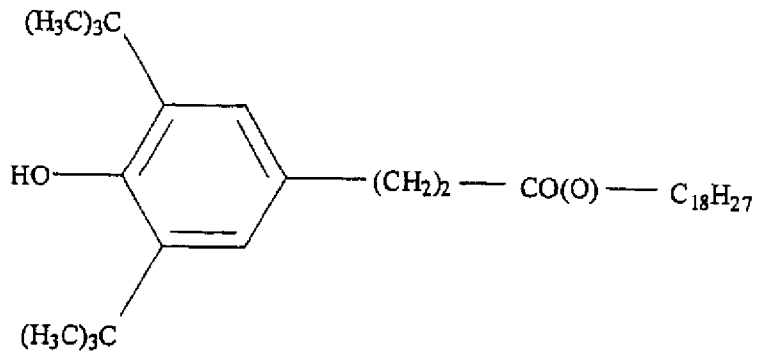

and should be shown as:

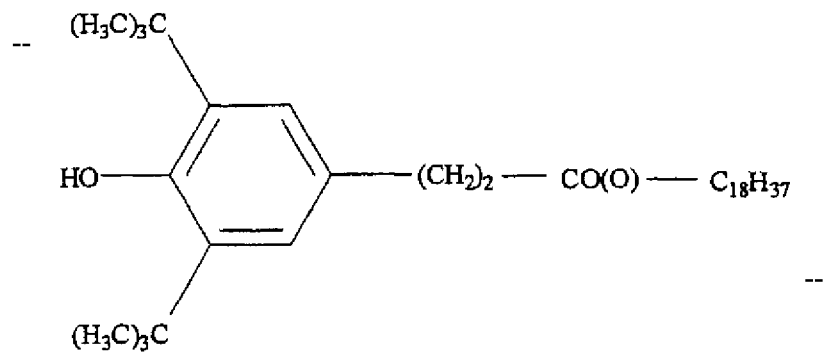

Signed and Sealed this

Thirty-first Day of August, 2010

David J. Kappos
*Director of the United States Patent and Trademark Office*